United States Patent
Hahn et al.

(10) Patent No.: US 8,608,678 B2
(45) Date of Patent: Dec. 17, 2013

(54) ORTHOPEDIC TECHNICAL DEVICE (75) Inventors: Tanja Hahn, Duderstadt (DE); Erik Albrecht-Laatsch, Göttingen (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 401 days.

(21) Appl. No.: 12/993,135

(22) PCT Filed: May 19, 2009

(86) PCT No.: PCT/DE2009/000688
§ 371 (c)(1),
(2), (4) Date: Nov. 17, 2010

(87) PCT Pub. No.: WO2009/140948
PCT Pub. Date: Nov. 26, 2009

(65) Prior Publication Data
US 2011/0137212 A1    Jun. 9, 2011

(30) Foreign Application Priority Data

May 20, 2008   (DE) .......................... 10 2008 024 746

(51) Int. Cl.
*A61F 5/00*   (2006.01)
(52) U.S. Cl.
USPC ................................................ 602/23; 602/5
(58) Field of Classification Search
USPC ............ 600/587, 595; 602/1, 2, 5, 12, 16, 23, 602/27; 604/24–65; 623/24–65
See application file for complete search history.

(56) References Cited

U.S. PATENT DOCUMENTS

| | | | |
|---|---|---|---|
| 4,703,445 A | 10/1987 | Dassler | |
| 5,062,856 A | 11/1991 | Sawamura et al. | |
| 6,755,870 B1 | 6/2004 | Biedermann et al. | |
| 2004/0225242 A1* | 11/2004 | Lidolt et al. | 602/16 |
| 2008/0140221 A1* | 6/2008 | Macomber et al. | 623/27 |
| 2008/0287834 A1 | 11/2008 | Pusch | |

FOREIGN PATENT DOCUMENTS

| | | |
|---|---|---|
| DE | 3405081 A1 | 8/1985 |
| DE | 3909672 A1 | 10/1989 |
| DE | 19859931 A1 | 7/2000 |
| DE | 69918273 T2 | 7/2005 |
| DE | 102005051496 A1 | 5/2007 |
| WO | 9944547 A1 | 9/1999 |
| WO | 2008033852 A2 | 3/2008 |

OTHER PUBLICATIONS

PCT International Search Report for International Application No. PCT/DE2009/000688, mailed Aug. 25, 2009.

* cited by examiner

*Primary Examiner* — Brian Szmal
*Assistant Examiner* — Megan Leedy
(74) *Attorney, Agent, or Firm* — Holland & Hart LLP (57) ABSTRACT

The invention relates to an orthopedic technical device for the lower extremities, with at least one receptacle (12, 16) for an extremity (14, 18), a sensor (30) and an electric evaluating unit (34), which is connected with the sensor (30) for processing data of a sensor (30). According to the invention, it is proposed that the electric evaluating unit (34) be set up in order to carry out a method with the following steps: (i) switching into a learning mode, (ii) determining at least one characteristic value of the system (R, S, N, $a_{w,threshold}$), (iii) storing the characteristic value of the system (R, S, N, $a_{w,threshold}$), (iv) switching into an operating method and (v), in the operating mode, influencing, optimizing or selecting a control algorithm of the orthopedic device by means of the characteristic value of the system (R, S, N, $a_{w,threshold}$).

15 Claims, 4 Drawing Sheets

ORTHOPEDIC TECHNICAL DEVICE

The invention relates to an orthopedic technical device for the lower extremities, with (a) at least one receptacle for an extremity, (b) a sensor, and (c) an electrical evaluation unit, connected to the sensor, for processing data from the sensor.

DE 39 09 672 A1 has disclosed a thigh prosthesis as per the preamble of claim 1. A disadvantage of such a thigh prosthesis is that it has to be taught in elaborately. By way of example, if the angle sensor is attached to the wrong side, teaching-in is impossible.

WO 99/44547 has disclosed a control unit for a prosthesis, which comprises a dynamically adaptable knee-movement control unit that changes the flexion and/or extension of the knee as a function of a variability of a kinematic parameter. What is also disadvantageous in this case is that this orthopedic technical device must be taught in elaborately and does not function if there is gross erroneous fitting of the sensor.

DE 10 2005 051 496 A1 has disclosed a method for carrying out functional analysis of an artificial extremity. This method sets in after an initial setup of the orthopedic technical device and improves the running methods. This document contains no teaching as to how to intervene quickly, even in the case of an erroneous fit of the sensor.

DE 34 05 081 A1 has disclosed a sports shoe for track events. A disadvantage of this sports shoe is that it is not suitable for use as an orthopedic technical device.

By way of example, such an orthopedic technical device can be an orthosis that is used to enable patients with residual muscular activity to walk despite their muscular strength not sufficing for normal walking. Orthopedic technical devices like such an orthosis comprise components that can be mass produced. However, individual components must be attached to one another and must be individually matched to the patient who is intended to wear the orthopedic technical device, for example by an orthopedic technician.

A disadvantage of known orthopedic technical devices is that it is complicated to set them up for the respective patient. Additionally, components can be fitted incorrectly. This lowers the patient's acceptance of the orthopedic technical device, and leads to costs and the risk of an incorrect setting resulting from operating errors. This can then lead to, for example, too late or too early activation of a locking and/or damping mechanism during the use of the orthotic orthopedic technical device, increasing the probability of an accident.

The invention is based on the object of configuring an orthopedic technical device such that it can be set up in a faster or more reliable fashion.

The invention achieves the object by a generic orthopedic technical device, in which the electrical evaluation unit is configured to carry out a method with the following steps: (i) switching into a learning mode, (ii) establishing at least one system characteristic value, (iii) storing the system characteristic value, (iv) switching into an operating mode, and (v) optimizing or selecting a control algorithm for the orthopedic technical device with the aid of the system characteristic value (R, S, N, $a_{W,threshold}$) in the operating mode.

An advantage of this orthopedic technical device is that it can be matched to a patient in a particularly simple fashion. Moreover, the simple and intuitive operability of the orthopedic technical device is advantageous. Hence, there are only few requirements for fitting the sensor onto the orthopedic technical device, and so even less qualified staff are suitable for fitting and adjusting this fit.

A further advantage is that the sensor can be attached at a multiplicity of positions without its function being impaired. This allows the sensor to be attached where it is of little annoyance to the patient. This increases the acceptance of the orthopedic technical device. By way of example, the sensor can also be arranged at a distance from the receptacle on the ankle or under the sole on a contralateral side.

An advantage of this orthopedic technical device is that the reliable functioning is not impaired by, for example, a fitting error made by the orthopedic technician.

Within the scope of the present description, the sensor is more particularly understood to be any mechanism that is set up and arranged to measure a position, direction, force or a torque. Processing data from the sensor is more particularly understood to mean that the data is used for open and/or closed loop control of a mechanism and/or is stored for later evaluation. By way of example, the torque value can be corrected when standing straight, when no torque should be exerted.

The learning mode could also be referred to as a calibration function. This calibration function is not limited to subsequent correction of sensor data. Alternatively, or in addition thereto, profiles can be selected that are assigned to the established system characteristic value. Moreover, amplification factors (gain), displacement factors (offset), linearity errors or thresholds can be established. Alternatively, or in addition thereto, patient-dependent characteristic values can moreover be established.

The control algorithm is more particularly understood to be a program that is stored in the evaluation unit and reads data measured by the sensor and for example outputs control commands to an actuator of the orthopedic technical device. The feature that the control unit is an evaluation unit for carrying out the specified steps is more particularly understood to mean that the evaluation unit has a digital storage medium in which program code is stored. This program code results in the control unit automatically carrying out the specified steps.

According to a preferred embodiment, the electrical evaluation unit is configured to carry out a method with the following steps: (i) switching into a learning mode, (ii) establishing at least one fitting-error characteristic value that encodes a fitting error of the sensor, (iii) storing the fitting-error characteristic value, (iv) switching into the operating mode, and (v) correcting sensor data with the aid of the at least one fitting-error characteristic value.

Here, a fitting-error characteristic value is more particularly understood to be a variable that encodes a deviation of an intended position and/or an intended location of the sensor from an actual position and/or an actual location of the sensor. By way of example, the deviation is due to the orthopedic technician not having attached the sensor at the intended site because they did not know the correct site or because attachment at the correct site was impossible. The actual position is that position that the sensor must assume for the electrical evaluation unit to function correctly without further corrections.

In a preferred embodiment, the sensor is an angle sensor for registering an inclination with respect to the vertical. The angle sensor is more particularly understood to be any mechanism that is designed and arranged to register its orientation with respect to the horizontal or the vertical, and to emit this in an encoded fashion in the form of a signal. By way of example, the angle sensor is a gravitational angle sensor that always supplies the precise angle to the center of the earth reference point. For this purpose, such a gravitational angle sensor has a unit registering the perpendicular.

The angle sensor can moreover comprise an electrical evaluation unit that generates the electrical inclination signal. The angle sensor registers its inclination with respect to the vertical or the horizontal, but this is only the inclination of the receptacle with respect to the vertical or to the horizontal actually to be measured if said angle sensor has been fitted correctly or if the measurement values have been corrected with the aid of the fitting-error characteristic value.

The locking and/or damping mechanism is more particularly understood to be any mechanical mechanism that can assume at least two switching states, namely an activated and a released switching state. In the activated switching state, pivoting of the thigh receptacle relative to the shank receptacle has been locked or has been made significantly more difficult by a damping element. Corresponding pivoting is possible in the released setting. The locking and/or damping mechanism can for example have a hydraulic or purely mechanical design.

The feature that the inclination signal is established as a function of the fitting-error characteristic value is more particularly understood to mean that raw measurement values, which encode the inclination of the angle sensor with respect to the horizontal or to the vertical, are corrected using the fitting-error characteristic value such that thereafter they encode the inclination of the thigh receptacle with respect to the horizontal or the vertical. In this context, it is irrelevant whether a position with respect to the horizontal or to the vertical is encoded because both statements contain equivalent information, namely the position of the thigh receptacle in space. By way of example, the angle at which the locking and/or damping mechanism opens or locks is fixedly prescribed in a conventional orthosis.

In a preferred embodiment, the fitting-error characteristic value is established while the locking and/or damping mechanism locks the thigh receptacle and the shank receptacle relative to one another, with both preferably being locked in a position of hyperextension. Advantageously, this position permits particularly risk-free and hence 8 comfortable setting-up of the actuation unit.

According to a preferred embodiment, the fitting-error characteristic value is a radial-error characteristic value that encodes a difference between a maximum value and a minimum value of the inclination signal. If the angle sensor is not fitted precisely laterally, but offset frontally or dorsally on the thigh receptacle, the difference between the maximum value and the minimum value of the inclination signal is reduced. By measuring this difference, and hence with the aid of the radial-error characteristic value, the inclination signal can be normalized with respect to a predefined intended difference.

Alternatively, or in addition thereto, the method preferably comprises the step of establishing an inclination-error characteristic value that encodes the minimum value or the maximum value of the electrical inclination signal when the electrical evaluation unit is in the learning mode, and storing the inclination-error characteristic value in the digital storage medium, with the inclination signal being established as a function of the inclination-error characteristic value in the operating mode of the electrical evaluation unit. This should be understood to mean that the inclination signal changes if the inclination-error characteristic value changes. By way of example, the inclination-error characteristic value is a normalization factor in a mathematical calculation formula.

Alternatively, or in addition thereto, a side-error characteristic value is established that encodes a sign of a change in the inclination signal when the thigh receptacle swings forward, and the side-error characteristic value is stored in the digital storage medium, with the inclination signal being established as a function of the side-error characteristic value in the operating mode. Here, forward swinging of the thigh receptacle is understood to mean a pivot movement in the sagittal plane in the frontal direction. As a result of this, it is possible to detect the fitting error that consists of the angle sensor having been arranged on the wrong side of the thigh receptacle. That is to say that, for example, an angle sensor intended for a left thigh receptacle has been fitted to a right thigh receptacle.

The orthopedic technical device should prevent the patient from buckling at the knee at the wrong time and suffering a fall as a result of this. It is therefore important for the locking and/or damping mechanism to be reliably closed when there is a danger of buckling. On the other hand, the locking and/or damping mechanism should be open when the leg swings through in a forward direction in order to allow comfortable wear. These requirements are satisfied particularly well if the electrical evaluation unit of the generic orthosis is configured to carry out a method with the following steps: (i) establishing the maximum value of the inclination signal, (ii) establishing a threshold, which is smaller than the maximum value, (iii) emitting an opening command to the locking and/or damping mechanism if the inclination signal drops below the threshold, (iv) registering whether the locking and/or damping mechanism is released, and (v) reducing the threshold if not, (vi) repeating to determine the threshold through to possibly reducing the threshold until the locking and/or damping mechanism is released, and (vii) storing the last threshold. Here, the last threshold is a fitting-error characteristic value. The aforementioned steps are carried out in the learning mode. In the operating mode the locking and/or damping mechanism locks or releases when this threshold is undershot or exceeded.

By way of example, the first threshold is established by establishing the difference between the maximum value and the minimum value. This difference is subsequently subdivided into a multiplicity of sections of, in particular, equal size, for example into ten or more sections. In the former case, the tenth section corresponds to the maximum value and the zeroth section corresponds to the minimum value. The ninth stage is then for example fixed as the first threshold. It is possible for more than ten stages to be provided. It is also possible for the stages not to be selected in an equidistant fashion.

A threshold particularly suited to obtaining an orthosis that is comfortable to wear is generated by establishing whether the locking and/or damping mechanism is released after a predetermined number of opening commands and after an associated number of steps of the patient with the orthosis. In the process, the steps of establishing the threshold through to possibly reducing the threshold are repeated for an unchanging threshold until the locking and/or damping mechanism is released during the predetermined number of opening commands. It is only after this that the last threshold is stored. This then ensures that the locking and/or damping mechanism always releases and locks in a timely fashion with a sufficiently high probability. The threshold established thus is a measure of the inclination with respect to the horizontal of the thigh receptacle at which the locking and/or damping mechanism opens.

A modularizable orthosis is obtained if the angle sensor is designed for calculating the inclination signal with the aid of the fitting-error characteristic value or the fitting-error characteristic values using a raw measurement value from a mechanism in a gravitational angle sensor that registers the perpendicular. By way of example, in this case the inclination signal can be a direct specification of the inclination at which the thigh receptacle is aligned with respect to the horizontal or the vertical. Such an inclination signal can be used particularly easily by the electrical evaluation unit for actuating the locking and/or damping mechanism to lock and to release.

The electrical evaluation unit is preferably configured to carry out a method with the step of emitting a signal, more particularly an acoustic or optical signal, prescribing a beat with which a user of the orthopedic technical device should walk with the orthopedic technical device.

Alternatively, or in addition thereto, the electrical evaluation unit is configured to output feedback relating to steps to be carried out by the operator. This feedback can be given via speech output or a display. In particular, the feedback can be instructions relating to a movement or gait to be carried out by the user, that is to say, for example, the instructions to walk slower, faster, more regularly, over steps, over a ramp or in circles.

The invention additionally achieves the object by a method for configuring an orthosis according to the invention comprising the following steps: (a) switching the orthosis into the learning mode, (b) moving the thigh receptacle into a forward-step position, (c) entering status information into the evaluation unit, which encodes the state that the thigh receptacle is in the forward-step position such that an electrical evaluation unit of the orthosis can establish a maximum value or a minimum value of the inclination signal, (d) moving the thigh receptacle into a standing position such that an electrical evaluation unit of the orthosis can correspondingly establish the minimum value or the maximum value of the inclination signal, (e) entering status information into the evaluation unit, which encodes the state that the thigh receptacle is in the standing position, and (f) entering status information into the evaluation unit where necessary, which encodes the state that input is complete.

In the following text, the invention will be explained in more detail with the aid of an exemplary embodiment, in which.

Figure 1:
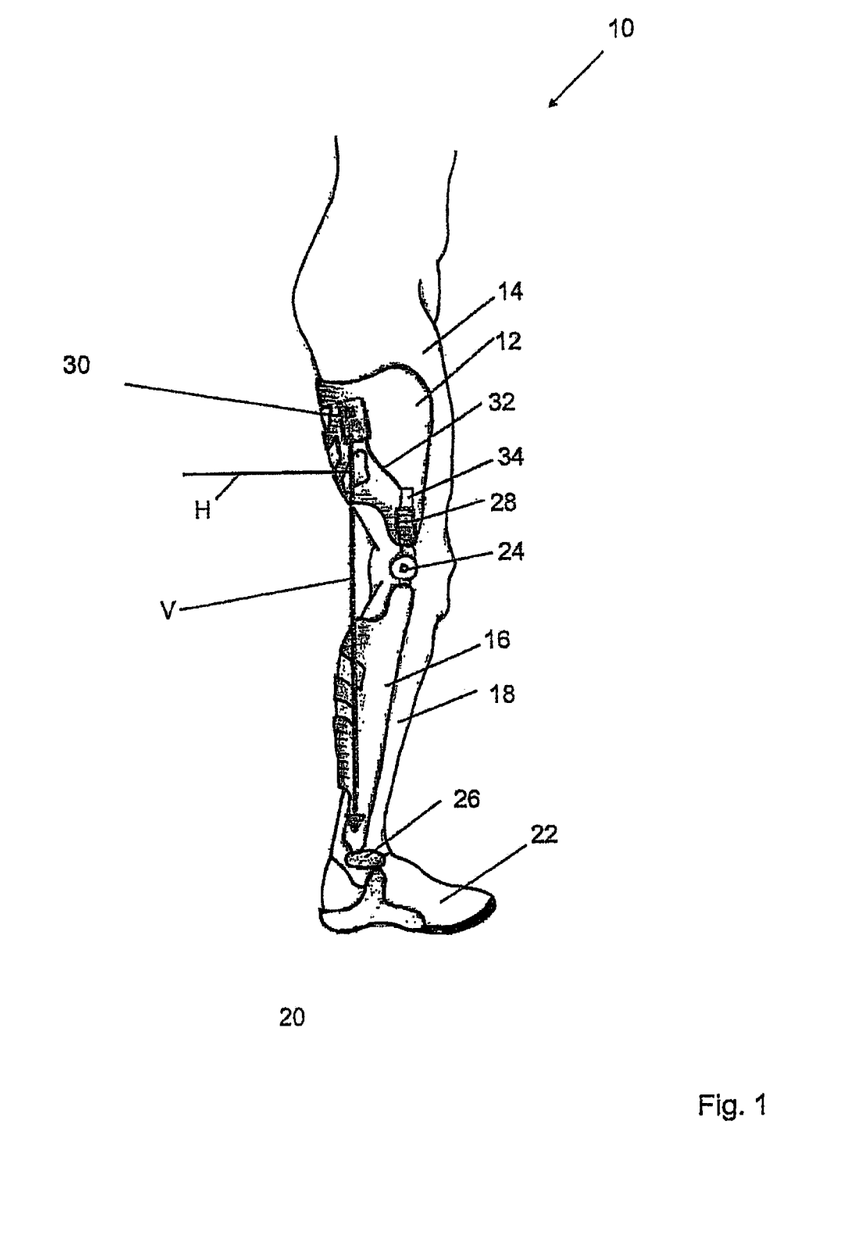
FIG. 1 shows an orthosis according to the invention.

FIG. 1 shows an orthosis 10, which comprises a first receptacle for an extremity in the form of a thigh receptacle 12 for holding a thigh 14, a second receptacle in the form of a shank receptacle 16 for holding a shank 18 and a third receptacle in the form of a foot receptacle 20 for holding a foot 22. The thigh receptacle 12 and the shank receptacle 16 are attached to one another in a pivotable fashion by means of a knee joint 24. The foot receptacle 20 is attached to the shank receptacle 16 in a pivotable fashion by means of a foot joint 26.

The knee joint 24 comprises a locking and/or damping mechanism in the form of a locking mechanism 28 that is designed to activate the knee joint 24 by locking, or to release the locking of the knee joint 24, on the basis of electrical actuation by an electrical control signal. The locking mechanism 28 is electrically connected to a sensor in the form of an angle sensor 30, which is attached laterally to a proximal end of the thigh receptacle 12.

The angle sensor 30 is a gravitational angle sensor designed to emit an electrical inclination signal $a_W$. The inclination signal $a_W$ encodes an inclination $\alpha_W$ that the angle sensor 30 assumes with respect to a vertical V. Alternatively, the inclination signal $a_W$ encodes an inclination that the angle sensor 30 assumes with respect to a horizontal H. The inclination $\alpha_W$ corresponds precisely to the inclination $\alpha_O$ of a zero position of the thigh receptacle 12 with respect to the vertical V if the angle sensor 30 has been fitted correctly to the thigh receptacle 12.

Figure 3:
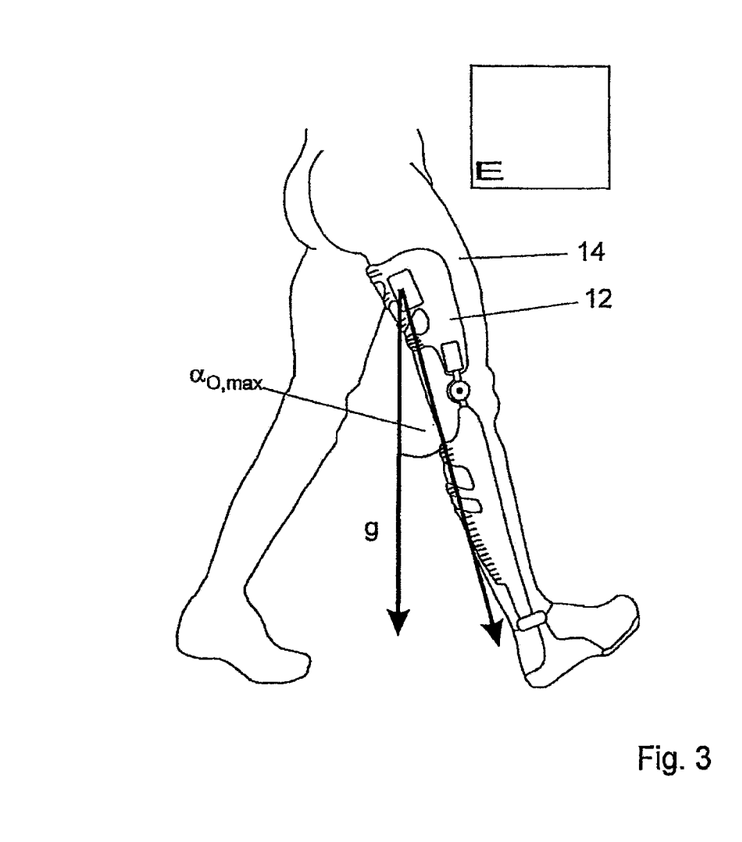
FIG. 3 shows the orthosis as per FIG. 1 in a forward-step position.
Figure 4:
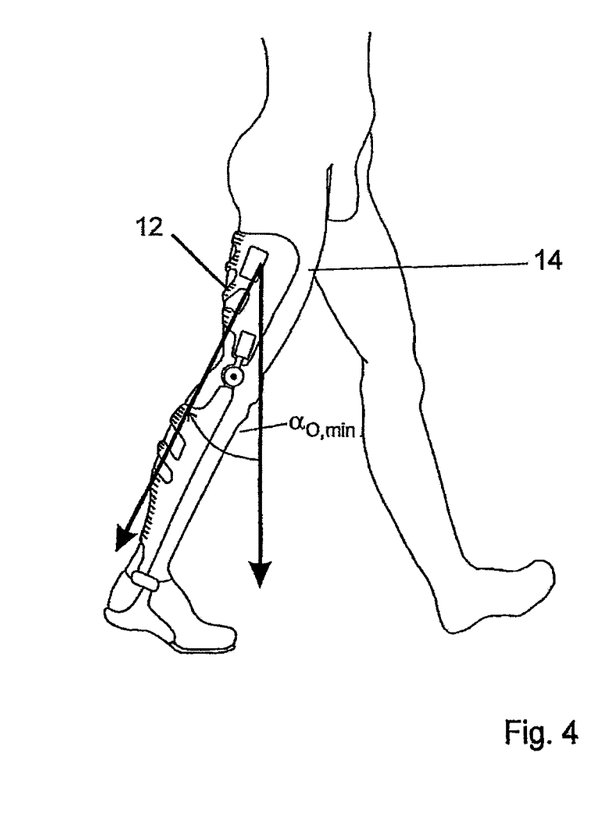
FIG. 4 shows the orthosis in an end-of-step position.

Whilst walking, the inclination $\alpha_O$ of the thigh receptacle 12 with respect to the vertical V changes between a maximum angle $\alpha_{O,max}$, as shown in FIG. 3, and a minimum angle $\alpha_{O,min}$, as shown in FIG. 4. Provided it has been fitted correctly, the angle sensor 30 continuously measures the inclination $\alpha_O$ by measuring the inclination $\alpha_W$ and sends the electrical inclination signal $a_W$, which for example encodes the inclination $\alpha_W$ in the form of a number, to a schematically illustrated electrical evaluation unit 34 of the locking mechanism 28.

The electrical evaluation unit 34 compares the inclination signal $a_W$ in the form of the number encoding the inclination $\alpha_W$ to a threshold $a_{W,threshold}$ representing an associated inclination $\alpha_{W,threshold}$ and thereupon locks the locking mechanism 28 or releases the latter. This ensures that the thigh receptacle 12 and the shank receptacle 16 are interconnected rigidly with respect to rotation when the patient loads their leg.

Figure 2:
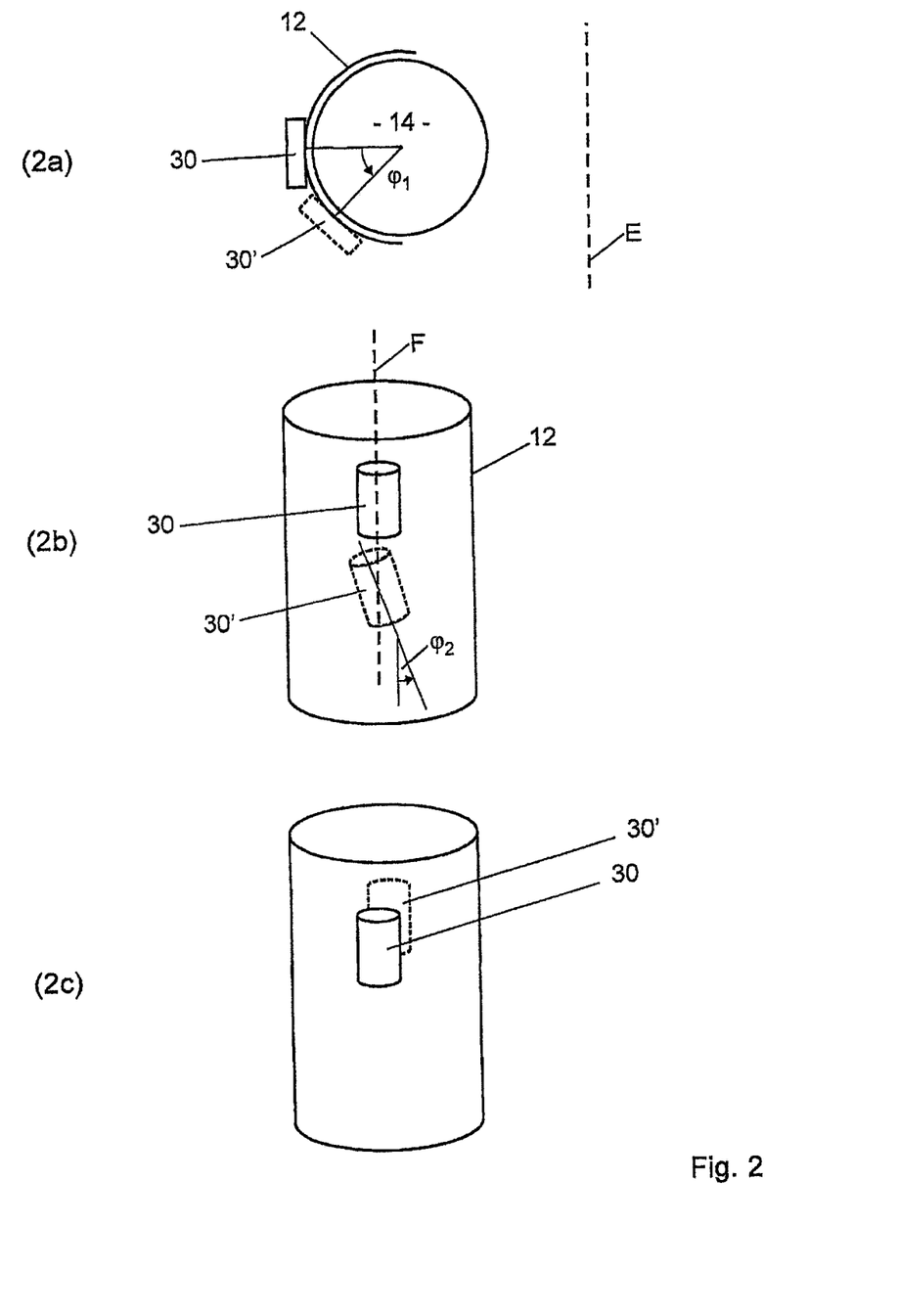
FIG. 2 shows three possible fitting errors of an angle sensor relative to the thigh receptacle of the orthosis as per FIG. 1 in three subfigures 2a, 2b and 2c.

Three sources of error can be distinguished when fitting the angle sensor 30. A first source of error is shown in subfigure 2a of FIG. 2. Whereas the angle sensor 30 shown with a solid line is arranged in a correct position, namely parallel to a sagittal plane E, the angle sensor 30' drawn with dashed lines is arranged incorrectly by an error angle $\phi_1$. During a walking movement, this leads to the inclination $\alpha_W$ measured by the angle sensor 30 varying between a maximum inclination $\alpha_{W,max}$ and a minimum inclination $\alpha_{W,min}$, with the magnitude of these angles being smaller than the maximum angle $\alpha_{O,max}$ or $\alpha_{O,min}$ between the thigh receptacle 12 and the vertical V. Further below describes how a radial-error characteristic value R can be established, with the aid of which the influence of the error angle $\phi_1$ is eliminated.

Subfigure 2b of FIG. 2 shows the case where the angle sensor 30 is fitted at a correct position on the thigh receptacle 12, whereas the angle sensor 30' illustrated by dashed lines has been fitted with an error angle $\phi_2$ relative to a frontal plane F. The angle sensor 30 emits an inclination $\alpha_W$, which differs from the correct inclination $\alpha_O$ by the error angle $\phi_2$. How to correct this error with the aid of an inclination-error characteristic value N is likewise described further below.

Subfigure 2c of FIG. 2 shows a third possible error, in which the angle sensor 30' has been arranged on the wrong side of the thigh receptacle 12. This error could also be considered an error as per subfigure 2a, in which the error angle $\phi_1$ is 180°.

The orthosis 10 according to the invention is configured as described in the following text. The electrical evaluation unit 34 is firstly switched into a learning mode. By way of example, this can be brought about by pressing an appropriate button on the evaluation unit 34. Alternatively, the evaluation unit comprises e.g. an infrared or ultrasound receiver, and an appropriate infrared or ultrasound signal is emitted by a remote control, and this signal switches the evaluation unit 34 into the learning mode.

Status information encoding that a side-error recognition mode should be initiated is subsequently entered into the evaluation unit 34. The thigh receptacle 12 is subsequently pivoted frontally in the sagittal plane E. By way of example, this can be brought about by the patient pivoting their thigh 14 forward. Status information encoding that the thigh receptacle 12 is in a forward-step position is entered into the evaluation unit 34 in this state.

The thigh receptacle 12 is subsequently brought into a standing position shown in FIG. 1 or an end-of-step position shown in FIG. 4, for example by the patient moving their thigh 14 accordingly. Once this has been reached, status information encoding the state that the thigh receptacle 12 is in the standing position or end-of-step position is entered into the evaluation unit 34. Entering a completion entry indicates to the evaluation unit 34 that the evaluation can be initiated.

Figure 5:
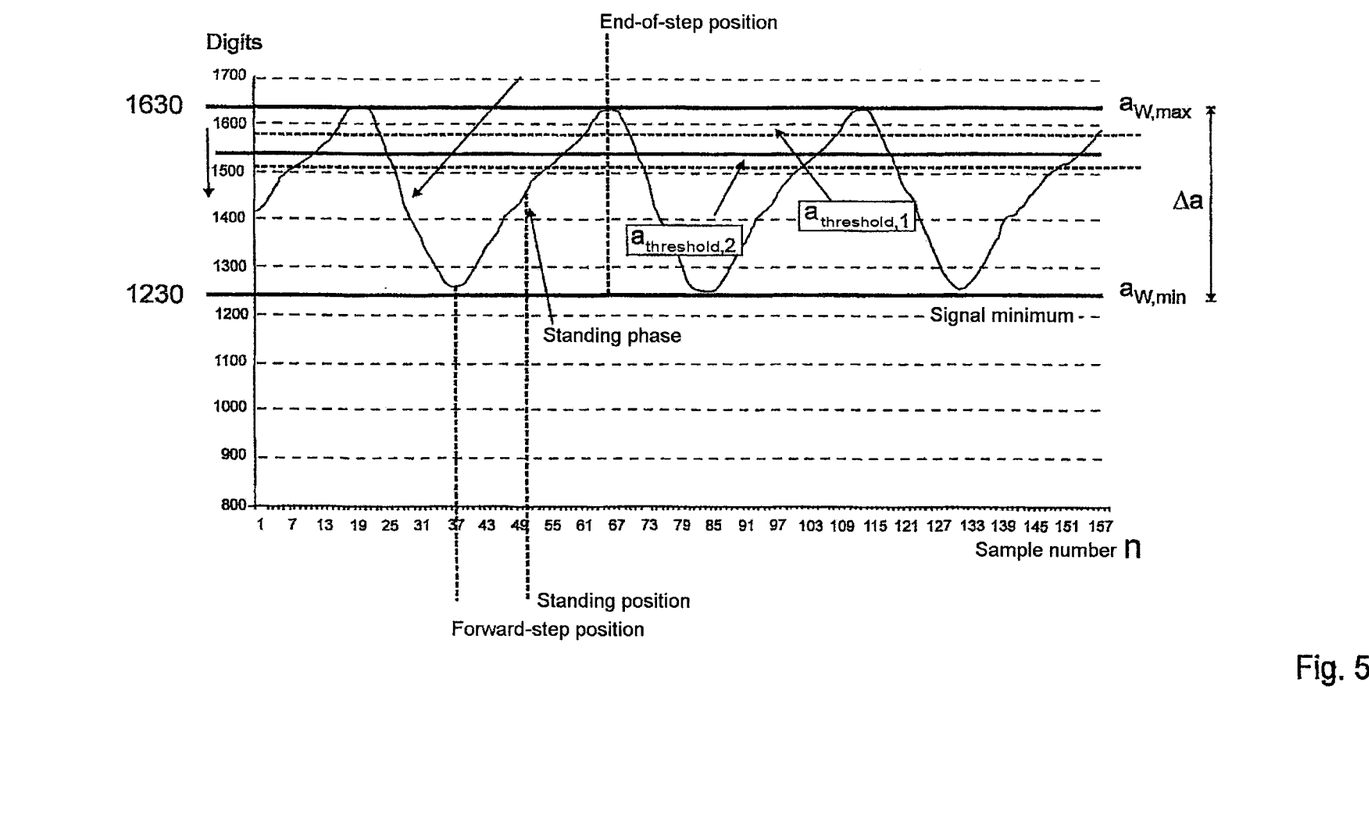
FIG. 5 shows a diagram plotting inclination signal as a function of time.

During the input, the angle sensor 30 has for example recorded the profile shown in FIG. 5. FIG. 5 shows, encoded as $a_W$, the inclination $\alpha_W$ of the angle sensor with respect to the vertical in counting units (digits). The sample number n represents a measure of time. At sample number 37, the status message was entered that the forward-step position has been reached. What was entered at sample number 62 is that the end-of-step position has been reached. This demonstrates that the angle sensor 30 has been attached to the correct side. If the angle sensor had been attached to the wrong side, the forward-step position would have been measured at 1630 digits and the end-of-step position at 1250 digits. The evaluation unit 34 thereupon stores a side-error characteristic value S in a digital storage medium that encodes the state that there is no side error.

The electrical evaluation unit 34 subsequently establishes a maximum value $a_{W,max}$ of the inclination signal and a minimum value $a_{W,min}$ of the inclination signal $a_W$, which can be converted into the associated inclinations $\alpha_{W,max}$ and $\alpha_{W,min}$. The difference $\Delta a$ is calculated from the maximum value $a_{W,max}$ and the minimum value $a_{W,min}$, which is $\Delta a = 1660 - 1250 = 410$ in the present case.

This difference $\Delta a$ can be subsequently calibrated with respect to a predefined value. It is particularly expedient for this purpose if the inclination $\alpha_O$ of the thigh receptacle 12 is set to a predefined value in the end-of-step position (FIG. 4) and in the forward-step position (FIG. 3), for example by using an external inclinometer. The difference $\Delta a$ represents a possible radial-error characteristic value R. The radial-error characteristic value R allows normalization of the inclination signal $a_W$ with respect to an intended difference.

The evaluation unit 34 subsequently stores the signal maximum $a_{W,max}$ and the signal minimum $a_{W,min}$ in the digital storage medium. A threshold at which the evaluation unit 34 locks or opens the knee joint 24 is subsequently established.

For this purpose, a first threshold $a_{W,threshold,1}$ is established by selecting it to be $a_{W,threshold,1} = a_{W,min} + 0.95 \Delta a$. The patient now walks with the orthosis and the evaluation unit 34 attempts to open the knee joint 24 when an inclination $\alpha_{W,threshold,1}$ corresponding to the inclination $\alpha_{W,threshold,1}$ has been reached. If there still is a load on the knee 24 at this time, the knee 24 cannot be released because the locking mechanism 28 was not designed with sufficient strength for this purpose. The evaluation unit 34 registers whether or not the knee 24 was released. If it was not released, the threshold is reduced, for example to the value $a_{W,Threshold,2} = a_{W,min} + 0.9 * \Delta a$.

This method is repeated until the electrical evaluation unit 34 is able, for the first time, to release the knee joint 24. Once this is the case, the respective threshold is kept constant until the knee joint opens correctly each time over a number of $n_G$ walk cycles, for example $n_G = 10$ walk cycles. Once this is the case, the corresponding threshold $a_{W,threshold,2}$ is written into the digital storage medium by the evaluation unit 34. As long as this is not the case, the threshold $a_{W,threshold}$ is reduced until the right threshold $a_{W,threshold}$ is found.

If the knee joint opens sporadically, the threshold can be reduced by a smaller amount than in the case where the knee 24 can never be released. Once the threshold $a_{W,threshold}$ has been found, the evaluation unit 34 automatically switches into the operating mode. Alternatively, or in addition thereto, the evaluation unit 34 is notified by an appropriate signal, for example by the push of a button or a remote control, that the learning mode has been completed. The evaluation unit 34 subsequently switches into the operating mode.

A threshold $a_{W,normal}$ and a difference $\Delta a_{normal}$ are to be expected if the angle sensor 30 has been fitted correctly and in the case of a natural gait. The threshold $a_{W,threshold}$ established as per the aforementioned method and the difference $\Delta a$ thus represent an inclination-error characteristic value N and a radial-error characteristic value R.

LIST OF REFERENCE SIGNS

10 Orthosis
12 Thigh receptacle
14 Thigh
16 Shank receptacle
18 Shank
20 Foot receptacle
22 Foot
24 Knee joint
26 Foot joint
28 Locking mechanism
30 Angle sensor
32 Electrical line
34 Evaluation unit
$\alpha_W$ Inclination angle sensor—vertical
$\alpha_O$ Inclination thigh receptacle—vertical
$\alpha_{W,max}$ Maximum angle
$\alpha_{W,min}$ Minimum angle
$a_W$ Inclination signal encoding the inclination $\alpha a_W$
$a_{W,threshold}$ Threshold
E Sagittal plane
F Frontal plane
H Horizontal
φ Error angle
R Radial-error characteristic value
S Side-error characteristic value
N Inclination-error characteristic value
$n_G$ Number of walk cycles
V Vertical

The invention claimed is:

1. An orthopedic technical device for the lower extremities, comprising:
    (a) a thigh receptacle for attachment to a thigh of a person,
    (b) an angle sensor to register an inclination with respect to the vertical and to emit an inclination signal,
    (c) an actuation device to release a switching command, and
    (d) an electrical evaluation unit, connected to the sensor, for processing data from the sensor, and to the actuation device,
    (e) wherein the electrical evaluation unit is configured to carry out a method with the following steps:
        (i) upon receiving the switching command from the actuation device, switching into a learning mode,
        (ii) establishing at least one fitting-error characteristic value that encodes a fitting error of the sensor,
        (iii) storing the fitting-error characteristic value,
        (iv) switching into an operating mode, and
        (v) correcting inclination sensor data from the angle sensor with the aid of the at least one fitting-error characteristic value in the operating mode.

2. The orthopedic technical device as claimed in claim 1, wherein the electrical evaluation unit is configured to establish the at least one fitting-error characteristic value only if it is in the learning mode.

3. The orthopedic technical device as claimed in claim 1, further comprising:
(a) a shank receptacle for attachment to a shank, and
(b) a locking and/or damping mechanism for releasably locking and/or damping a relative movement between thigh receptacle and shank receptacle,
(c) wherein the orthopedic technical device is an orthosis, and
(d) wherein the electrical evaluation unit has a digital storage medium and is designed to actuate the locking and/or damping mechanism as a function of the inclination signal in the operating mode for activating and for releasing the locking and/or damping mechanism and to carry out a method with the following steps:
(i) switching into the learning mode,
(ii) establishing the fitting-error characteristic value that encodes a positional deviation between a correct position of the angle sensor and an actual position of the angle sensor,
(iii) storing the fitting-error characteristic value in the digital storage medium, and
(iv) activating and releasing the locking and/or damping mechanism with the aid of the fitting-error characteristic value in the operating mode.

4. The orthopedic technical device as claimed in claim 3, wherein the electrical evaluation unit is configured to change the fitting-error characteristic value only when it is in the learning mode.

5. The orthopedic technical device as claimed in claim 3, wherein the electrical evaluation unit is configured to activate the locking and/or damping mechanism and to establish the fitting-error characteristic value while the locking and/or damping mechanism locks or are damped the thigh receptacle and the shank receptacle relative to one another.

6. The orthopedic technical device as claimed in claim 3, wherein a system characteristic value is a fitting-error characteristic value that encodes a fitting error of the sensor.

7. The orthopedic technical device as claimed in claim 3, wherein the electrical evaluation unit is configured to carry out a method with the following steps:
(i) establishing a fitting-error characteristic value in the form of an inclination-error characteristic value that encodes the minimum value or the maximum value of the electrical inclination signal after switching into the learning mode, and
(ii) storing the inclination-error characteristic value in the digital storage medium,
(iii) wherein the locking and/or damping mechanism is activated and released on the basis of the inclination-error characteristic value in the operating mode.

8. The orthopedic technical device as claimed in claim 3, wherein the electrical evaluation unit is configured to carry out a method with the following steps:
(i) establishing a fitting-error characteristic value in the form of a side-error characteristic value that encodes a sign of a change in the inclination signal when the thigh receptacle swings forward, and
(ii) storing the side-error characteristic value in the digital storage medium,
(iii) wherein the locking and/or damping mechanism is locked and released on the basis of the side-error characteristic value in the operating mode.

9. The orthopedic technical device as claimed in claim 3, wherein the electrical evaluation unit is configured to carry out a method with the following steps:
emitting a signal prescribing a beat with which a user of the orthopedic technical device should walk with the orthopedic technical device.

10. The orthopedic technical device as claimed in claim 3, wherein the electrical evaluation unit is configured to emit an instruction to the user to walk with a prescribed gait.

11. A method for configuring an orthopedic technical device as claimed in claim 1, comprising:
(i) after switching into a learning mode,
(ii) moving the orthopedic technical device such that at least one fitting-error characteristic value can be established,
(iii) entering status information into the evaluation unit which encodes that state that the fitting-error characteristic value should be stored, and
(iv) entering status information into the electrical evaluation unit, which encodes the state that a switch into the operating mode should be taken.

12. The method as claimed in claim 11, comprising the steps of:
(a) moving the thigh receptacle into a forward-step position,
(b) entering status information into the evaluation unit, which encodes the state that the thigh receptacle is in the forward-step position such that an electrical evaluation unit of the orthosis can establish a maximum value or a minimum value of the inclination signal,
(c) moving the thigh receptacle into a standing position such that the electrical evaluation unit of the orthosis can correspondingly establish the maximum value or the minimum value of the inclination signal,
(d) entering status information into the evaluation unit, which encodes the state that the thigh receptacle is in the standing position, and
(e) entering status information into the evaluation unit, which encodes the state that input is complete.

13. An orthopedic technical device for the lower extremities, comprising:
(a) a thigh receptacle for a thigh,
(b) a shank portion that is pivotable with respect to said thigh receptacle,
(c) a sensor for registering an inclination with respect to the vertical and for emitting an inclination signal,
(d) a locking and/or damping mechanism for releasably locking and/or damping a relative movement between said thigh receptacle and said shank portion, and
(e) an electrical evaluation unit, connected to said sensor, for processing data from said sensor,
(f) wherein said electrical evaluation unit is configured to carry out a method with the following steps:
switching into a learning mode,
establishing at least one fitting-error characteristic value that encodes a fitting error of said sensor,
storing said fitting-error characteristic value,
switching into an operating mode, and
correcting sensor data with the aid of said at least one fitting-error characteristic value in said operating mode,
(g) wherein establishing said fitting-error characteristic value comprises the following steps:
(i) establishing a maximum value of said inclination signal,
(ii) establishing a threshold, which is smaller than said maximum value,
(iii) emitting an opening command to said locking and/or damping mechanism if said inclination signal drops below said threshold, (iv) registering whether said locking and/or damping mechanism is released, and reducing said threshold if not, (v) carrying out steps (ii) to (v) until said locking and/or damping mechanism is released, and (vi) storing said fitting-error characteristic value in the form of said last threshold.

14. The orthopedic technical device as claimed in claim 13, wherein the electrical evaluation unit is configured to carry out a method with the following steps:

establishing a minimum value of said inclination signal, and storing the last threshold if said last threshold is less than 0.9 times an average between said maximum value and said minimum value.

15. The orthopedic technical device as claimed in claim 13, wherein the electrical evaluation unit is configured to carry out a method with the following steps:

establishing whether said locking and/or damping mechanism is released during predetermined number of opening commands, and carrying out steps (ii) to (v) as per claim 13 for an unchanging threshold until said locking and/or damping mechanism is released during said predetermined number of opening commands, before said last threshold is stored.

* * * * *